United States Patent
Ichida et al.

(10) Patent No.: US 7,317,071 B2
(45) Date of Patent: Jan. 8, 2008

(54) PROCESS FOR PRODUCING FLUOROMONOMER

(75) Inventors: Takuya Ichida, Osaka (JP); Yukio Homoto, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 26 days.

(21) Appl. No.: 10/506,008

(22) PCT Filed: Feb. 27, 2003

(86) PCT No.: PCT/JP03/02183

§ 371 (c)(1),
(2), (4) Date: Aug. 30, 2004

(87) PCT Pub. No.: WO03/074456

PCT Pub. Date: Sep. 12, 2003

(65) Prior Publication Data

US 2006/0020106 A1 Jan. 26, 2006

(30) Foreign Application Priority Data

Mar. 1, 2002 (JP) ............................. 2002-055914

(51) Int. Cl.
*C08F 6/00* (2006.01)
(52) U.S. Cl. ...................... 528/480; 422/131; 570/164; 570/165; 570/166; 570/167

(58) Field of Classification Search ................. 422/131; 528/480; 570/166, 167, 164, 165
See application file for complete search history.

(56) References Cited

U.S. PATENT DOCUMENTS

| 3,832,411 | A | * | 8/1974 | Arkles et al. ................. 570/152 |
| 4,391,763 | A | * | 7/1983 | Ueno et al. ..................... 264/15 |
| 5,432,259 | A | | 7/1995 | Schottle et al. |
| 5,705,719 | A | | 1/1998 | Bloos et al. |
| 5,902,912 | A | * | 5/1999 | Tung et al. .................. 570/164 |

FOREIGN PATENT DOCUMENTS

| JP | 40-24026 | | 10/1965 |
| JP | 47-16405 | | 9/1972 |
| JP | 54-154710 | * | 6/1979 |
| JP | 54-154710 A | | 12/1979 |
| JP | 7-188073 A | | 7/1995 |

OTHER PUBLICATIONS

Przemysl Chemiczny 66/7 (1987) p. 333 to 335.

* cited by examiner

*Primary Examiner*—Terressa Boykin
(74) *Attorney, Agent, or Firm*—Birch, Stewart, Kolasch & Birch, LLP

(57) ABSTRACT

Processes for producing a fluoromonomer from a fluoropolymer, among which one that can be carried out more simply is a process wherein thermal decomposition of a fluoropolymer is preformed by means of a rotary kiln (5) so as to produce a fluoromonomer, the process comprising feeding a fluoropolymer and steam (3) into a rotary kiln and heating the fluoropolymer.

9 Claims, 1 Drawing Sheet

PROCESS FOR PRODUCING FLUOROMONOMER

This application claims priority under 35 U.S.C. §119 of Japanese Application No. 2002-055914, filed Mar. 1, 2002, and this application is the National Stage of PCT/JP03/02183, filed Feb. 27, 2003, the contents of which applications are hereby incorporated by reference.

1. Technical Field

The present invention relates to a process for producing a fluoromonomer by thermally decomposing a fluoropolymer in the presence of steam. The produced fluoromonomer is used for producing a fluoropolymer.

2. Background Art

Due to the high market value of a fluoropolymer, it is desirable to recycle a fluoropolymer such as polytetrafluoroethylene (referred to also as "PTFE") as much as possible. For example, U.S. Pat. No. 3,832,411 discloses a process wherein tetrafluoroethylene (referred to also as "TFE") as the fluoromonomer is recovered from PTFE as the fluoropolymer by thermally decomposing PTFE at a high temperature. In this process, the polytetrafluoroethylene supported by a perforated metal plate is heated to be thermally decomposed by means of high temperature steam. This process produces tetrafluoroethylene at a high concentration, however, it can be carried out only in a batch mode.

A thesis written by Halina Miesowicz (Przemysl Chemiczny, 1987, 66/7, 333-335) also discloses a process wherein polytetrafluoroethlene is thermally decomposed in a steam atmosphere. In this process, a PTFE mass (of which size is 2-3 mm) is thermally decomposed in a batch mode at an approximately atmospheric pressure and a temperature of from 550° C. to 700° C. According to the thesis, when a mass ratio of the PTFE to the steam is 1 to 10 or 1 to 15, a gas having a TFE content of from 79 to 88 mass % and a hexafluoropropylene (referred to also as "HEF") content of from 5 to 9 mass % is produced, and at the same time, a low molecular weight polymer of 4-9 weight % in the powder form is produced and deposited as a solid by-product. Such thesis teaches that there is a possibility that perfluoroisobutene (referred to also as "PFIB") is produced. This compound has a strong toxic effect, so that it is desirable to suppress a production thereof.

It is known that PFIB is produced when TFE is thermally decomposed to produce HFP (See, for example, Japanese Patent Kokoku Publication No. 24026/1965 and U.S. Pat. No. 5,705,719). According to those patent references, a mole ratio of PFIB to HEP, both of which are produced by thermally decomposing the TFE, is approximately 1 to 5.

Above-mentioned deposit of the low molecular weight polymer as the solid by-product in the apparatus may cause various problems. Especially, the deposit of the polymer in a pipe may cause such a problem that the pipe is blocked with the deposited polymer so that an operation could not be continued any more. The low molecular weight polymer itself also leads to reduction of a recovery ratio of the fluoromonomer. Therefore, in order to thermally decompose the fluoromonomer stably and efficiently, it is desirable to suppress the production of such a solid by-product.

Japanese Patent Kokai Publication No. 188073/1995 discloses a process wherein a fluoropolymer is thermally decomposed in a fluidized bed to produce a fluoromonomer. In this process, the polymer and an inert particulate material are fluidized by means of steam to thermally decompose the fluoropolymer at a temperature of from 500° C. to 900° C. In general, it is not necessarily easy to operate the fluidized bed in terms of the stability thereof. This publication points out a technical problem upon its filing that a low thermal decomposition temperature (e.g. 650° C.) gives rise to a waxy product and then it adheres to a wall, which, in turn causes a clogging of the apparatus. This waxy product is also a low molecular weight polymer, and a solid by-product similar to the above-mentioned low molecular weight polymer in the powder form (except for the difference in their molecular weights). Such solid by-products are hereinafter collectively referred to as "oligomer(s)".

DISCLOSURE OF INVENTION

The processes for producing the fluoromonomer from the fluoropolymer, which are already known as mentioned above, are not necessarily satisfactory. Therefore, it is expected to provide a new process, preferably a process that is carried out more easily, more preferably a process that alleviates the problems which may be caused in the above-mentioned processes.

After careful consideration for the purpose of solving the above-mentioned problems, it has been found that it is a rotary kiln that enables to effectively produce a fluoromonomer by means of the thermal decomposition of a fluoropolymer in the presence of steam. The thermal decomposition by using of the rotary kiln will provide such an advantage that a steady and continuous operation is very readily performed, compared with that by using of the fluidized bed.

The present invention therefore provides a process for producing a fluoromonomer by thermally decomposing a fluoropolymer in a rotary kiln, wherein the fluoropolymer and steam are supplied to the rotary kiln so that the fluoropolymer is heated to a temperature which is not lower than a temperature at which the thermal decomposition thereof occurs. In accordance with the process of the present invention, a fluoropolymer derived from TFE is thermally decomposed, and a resulting fluoromonomer generally contains HEP and octafluorocyclobutane ($C_4F_8$, referred to also as "C-318") in addition to TFE.

Therefore, the present invention provides a process for producing TFE by thermally decomposing a fluoropolymer derived from TFE in a rotary kiln, wherein the fluoropolymer and steam are supplied to the rotary kiln so that the fluoropolymer is heated to a temperature which is not lower than a temperature at which the thermal decomposition thereof occurs. Furthermore, the present invention provides a process for producing HFP in a rotary kiln, wherein a fluoropolymer and steam are supplied to the rotary kiln so that the fluoropolymer is heated to a temperature which is not lower than the temperature at which the thermal decomposition thereof occurs.

Figure 1:
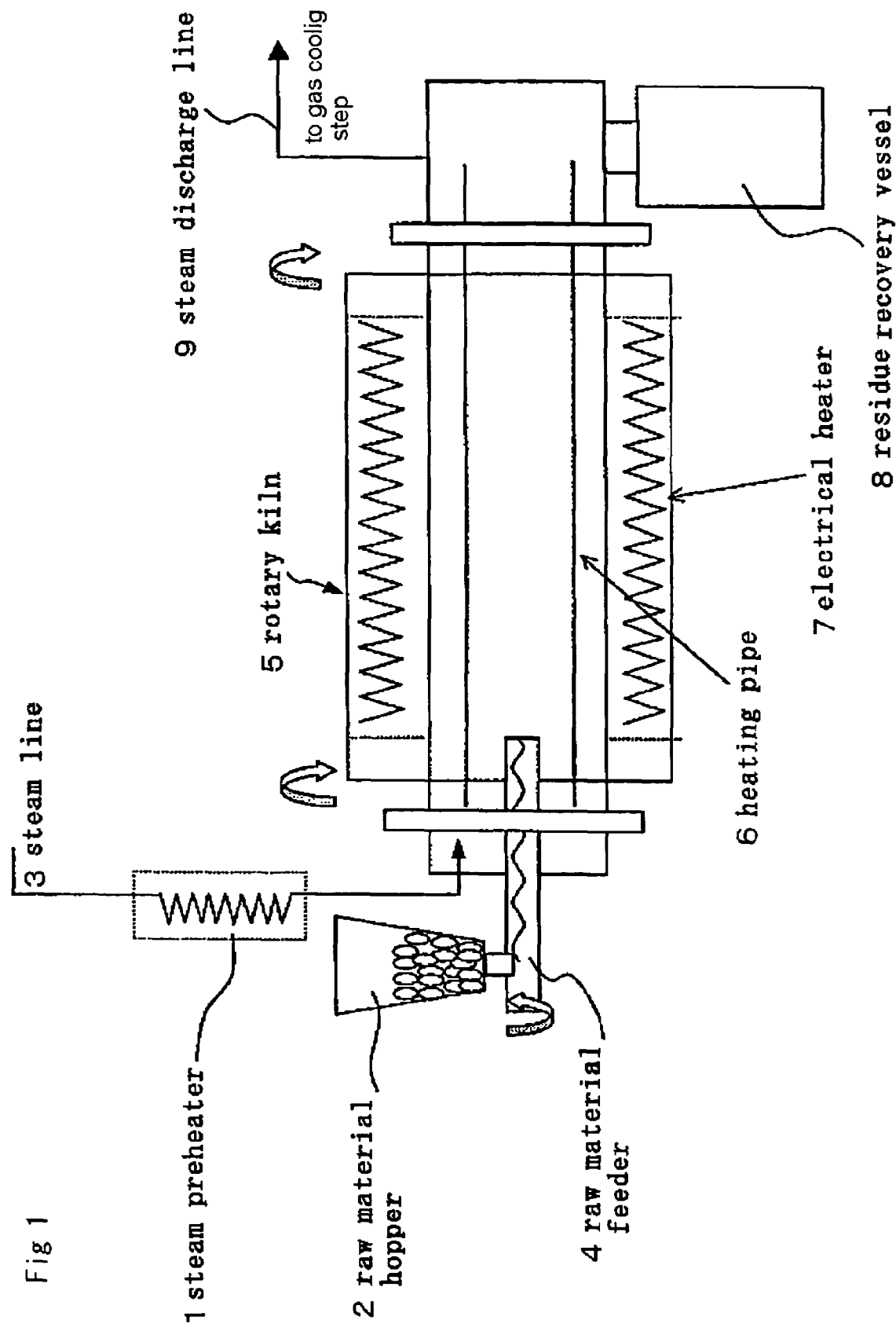
FIG. 1 shows a schematic flow sheet of an apparatus for carrying out a process according to the invention. In the drawing, the reference numbers correspond to the following elements.

1 . . . steam preheater, 2 . . . hopper, 3 . . . steam line, 4 . . . feeder, 5 . . . rotary kiln furnace, 6 . . . heating pipe, 7 . . . electrical heater, 8 . . . residue recovery vessel, and 9 . . . steam discharge line.

MODES FOR CARRYING OUT THE INVENTION

In one embodiment of the present invention, the fluoromonomer is kept within the rotary kiln at a temperature which is not lower than a temperature that enables a fluoropolymer to be thermally decomposed, and the fluoromonomer is produced. The produced fluoromonomer is entrained with the steam supplied to the rotary kiln, so that the fluoromonomer is discharged from the rotary kiln. The temperature at which the fluoropolymer is kept in that way is hereinafter referred to as a "thermal decomposition temperature (i.e. the temperature which is not lower than the temperature at which the thermal decomposition can occur, and at which the thermal decomposition is actually occurring)". Such thermal decomposition temperature may generally be assumed to be a temperature of an atmosphere within the rotary kiln. Such thermal decomposition temperature is achieved generally by heating the rotary kiln from its exterior (particularly from its wall surface), and the steam supplied to the rotary kiln optionally facilitates the achievement of such thermal decomposition temperature.

The rotary kiln has therein a cylindrical heating region. The temperature of the atmosphere within the rotary kiln herein used is represented by a temperature determined at the center of a cross-section (substantially circular cross-section) perpendicular to the longitudinal direction of such cylindrical heating region in the center of the heating region in terms of such longitudinal direction. Therefore, such temperature is hereinafter referred to as a "center temperature". In other words, the temperature of the atmosphere within the rotary kiln is represented by a temperature determined at a point on a rotational axis of the kiln, which point is located at the center of an entire length of the kiln, and such temperature corresponds to the thermal decomposition temperature in accordance with the process of the present invention. Therefore, the thermal decomposition temperature means the center temperature of the rotary kiln when the fluoropolymer is thermally being decomposed in accordance with the process of the present invention.

With respect to the temperature of the atmosphere within the rotary kiln, it is not necessarily the case that all of the temperatures determined along the direction of the rotational axis of the rotary kiln are substantially the same as the center temperature. In fact, they may be substantially different from the center temperature. When they are different, other temperatures (i.e. the temperatures except for the center temperature) of the heating regions along the direction of the rotational axis within the kiln may be normally within the ±20° C. range of the center temperature, preferably within the ±10° C. range of that, more preferably within the ±5° C. range of that. However, it is the most preferred case when the temperatures determined along the rotational axis of the rotary kiln are substantially the same (e.g. within ±2° C. range of the center temperature).

As mentioned above, the steam serves to supplementarily achieve the thermal decomposition temperature of the fluoropolymer as well as to entrain the produced fluoromonomer, whereby discharging it from the interior of the system. Therefore, the steam is usually supplied to the rotary kiln in a superheated condition. When the steam is required to help achieving a necessary thermal decomposition temperature, a temperature of the steam decreases within the rotary kiln from the temperature when supplied. Nevertheless, the steam discharged from the rotary kiln is in the superheated condition. As is often the case, when the rotary kiln has a sufficient heating capacity, the temperature of the superheated steam does not substantially change, and in some cases, the steam may be discharged from the rotary kiln with a temperature thereof slightly increased.

In accordance with the process of the present invention, the temperature of the rotary kiln, that is to say, the thermal decomposition temperature of a fluoropolymer is more than or equal to a temperature (normally 500° C.) that enables a fluoropolymer to be thermally decomposed. It is preferably more than or equal to 570° C. (e.g. 600° C. or over), more preferably more than or equal to 620° C. (e.g. 650° C. or over). In general, as long as there is no constraint on other factors (e.g. the problems concerning a heat resistance of the materials used for the rotary kiln), a high thermal decomposition temperature is preferred. The thermal decomposition temperature is normally performed up to 700° C., preferably up to 680° C., more preferably up to 670° C. The pressure in the rotary kiln, which is not necessarily limited, may be normally from 0.01 MPa to 1.0 MPa, for example from 0.02 MPa to 0.1 MPa.

In accordance with the process of the present invention, a fluoropolymer is thermally decomposed. However, all amount of the fluoropolymer is not necesarily decomposed into a fluoromonomer, so that a decomposition product contains a low molecular weight fluoropolymer, i.e. oligomer. When such oligomer is kept at a thermal decomposition temperature thereof, it may become a lower molecular weight fluoropolymer, and at the same time a fluoromonomer is also produced. The temperature, which is subjected to such an event that the produced oligomer is entrained with the steam in the rotary kiln to be discharged therefrom, is usually above a temperature that enables the oligomer to be thermally decomposed in the course of the above event. Therefore, the oligomer is further decomposed while it is being retained in the rotary kiln, entrained with the steam. As a result of that, an overall yield of the fluoromonomer is increased. Such oligomer corresponds to a solid by-product as described in relation to the prior art.

In view of that, a long average residence time of the steam within the rotary kiln is desirable as long as there is no constraint on other factors (e.g. too large volume of the rotary kiln). In accordance with the process of the present invention, an average residence time of the steam in the rotary kiln is at least 5 seconds (e.g. 8 seconds or over), at least 10 seconds or over (e.g. 25 seconds or over), more preferably 40 seconds or over (e.g. 50 or 60 seconds or over). Concretely speaking, the process is operated with the residence time of from 10 to 30 seconds, which is particularly preferred condition of the process when combined with the thermal decomposition temperature of from 620° C. to 670° C. The value, which is obtained by dividing a void volume of the rotary kiln (i.e. the void volume when a kiln interior is empty) by a volumetric flow rate (based on the volumetric flow rate at the inlet of the kiln) of the steam supplied to the rotary kiln, is hereinafter used as an average residence time. In this regard, however, when there exists an inert solid such as an inorganic particulate matter (as mentioned below) during the thermal decomposition, the above-mentioned void volume is a value obtained by subtracting a volume of such inert solid from the void volume of the rotary kiln. A nitrogen together with steam may be supplied so as to adjust the residence time, and in this case the average residence time is shorter according to the amount of the supplied nitrogen.

In accordance with the process of the present invention, the fluoropolymer to be thermally decomposed is a polymer produced from a fluorine-containing monomer, that is to say, a fluorine-containing polymer with fluorine resin and fluorine rubber. The polymer may be a homopolymer or a copolymer. The polymers suitable for the process of the present invention include a polymer derived from tetrafluoroethylene(TFE) such as polytetrafluoroethylene, TFE/perfluoroalkylvinylether copolymer called PFA, TFE/hexafluoropropylene copolymer called FEP, polyvinylidene fluoride/hexafluoropropylene copolymer (referred to also as "fluorine rubber") and polychlorotrifluoroethylene (referred to also as "PCTFE").

A fluoropolymer which can be used for the process of the present invention may be chips, or powder associated with the machining or defective products, all of which are derived from a formation of the fluoropolymer, or the recovered waste material and the like. Therefore, the process of the present invention provides a substantial process for recycling a fluoropolymer. Also, it is preferred that a fluoropolymer used for the process of the present invention, which is prior to being thermally decomposed, is small in size, e.g. in particulate form. Therefore, a pretreatment such as a pulverization treatment is carried out if needed. It is a preferred size that the longest diameter is 2-5 mm, for example.

In accordance with the process of the present invention, a fluoromonomer produced by the thermal decomposition is a fluoromonomer usable for producing a fluoropolymer. Such monomer mainly consists of tetrafluoroethylene. However, it is common that other fluoromonomers such as HFP and C-318 are also produced during the thermal decomposition. These other fluoromonomers include not only a fluoromonomer that is directly produced by the thermal decomposition of a fluoropolymer but also a fluoromonomer produced as a consequence of the thermal decomposition of TEF. Therefore, at the same time, the toxic PFIB is produced during the thermal decomposition. In addition to these monomers, carbon dioxide and the above-mentioned oligomer (i.e. the solid by-product that is solidified due to a decrease in a temperature) are also produced during the thermal decomposition of the fluoropolymer.

The used rotary kiln may be one that is generally used in the field of the industrial waste treatment and the like. Such a rotary kiln may be one that can treat a fluoropolymer in a continuous mode or in a batch mode. As a thermal decomposition is performed in the presence of steam, the steam is continuously supplied to the rotary kiln, and concomitantly, the steam containing a produced fluoromonomer and the like is continuously discharged from the rotary kiln.

It is preferred that the used steam is such that a thermal decomposition temperature is achieved, and that the produced fluoromonomer and the like are entrained off the rotary kiln. In general, the superheated steam is used as steam. For example, the steam having a temperature of from 400 to 800° C. may be used. The produced monomers and the like are separated from the steam by cooling the steam discharged from the rotary kiln, and then removing a resulting condensed water. Then, the fluoromonomer is purified by a separation if needed. The resulting fluoromonomer can be useful for a subsequent application.

The amount of the supplied steam, which is not limited, is such that a predetermined thermal decomposition temperature is achieved. For example, the supplied steam normally has a 0.4-5 fold mass relative to the mass of the supplied fluoropolymer, preferably 0.6-3.0 fold mass relative to that, more preferably 0.8-1.2 fold mass relative to that, so that the thermal decomposition of the fluoromonomer is continuously achieved.

For the purpose of improving an efficiency of the thermal decomposition in the rotary kiln, it is preferred that, together with a fluoropolymer, an inert solid, particularly a particulate matter, more particularly an inorganic particulate matter is provided in the rotary kiln. The heat supply to a fluoropolymer can be achieved more efficiently by supplying, for example, sand, glass, ceramic, metal or metallic oxides and the like to the rotary kiln together with the fluoropolymer. It is preferred that the inert solid is used, the mass of which is 0.1-10 fold weight relative to the mass of a fluoropolymer, particularly 0.5-3 fold weight relative to that. It is also preferred that the inert solid is approximately the same size as a fluoropolymer.

As mentioned above, with respect to the temperature of the rotary kiln, i.e. the decomposition temperature (T(K), absolute temperature) as well as the average residence time (t second), the higher or longer each of them becomes, the more preferable from a qualitative standpoint a thermal decomposition of a fluoropolymer for producing a fluoromonomer becomes. On the other hand, the lower or shorter each of them becomes, the more preferable from a industrial standpoint the thermal decomposition becomes. Considering those two contrary concepts, it is preferred that the process of the present invention is carried out under such a condition that the product (i.e. T×t) of the decomposition temperature (T(K)) and the average residence time (t seconds) is at least 9000 (K·seconds), more preferably at least 20000(K·seconds).

The decomposition product, which is obtained by thermally decomposing a fluoropolymer derived from TFE, has, for example, TFE content of 20-60 wt %, HFP content of 10-30 wt %, and C-318 content of 20-60 wt % with a small amount of carbon dioxide and PFIB, wherein the wt % is based on the gas (25° C.) obtained by removing the condensed steam. Due to the thermal decomposition, the product includes the above-mentioned oligomer. When the steam supply line is cooled, particularly quenched, such oligomer is adhered to the wall surface thereof as a solid by-product. The amount of the adhered oligomer is considerably small, usually at most 10 wt % relative to the fluoropolymer to be decomposed, preferably 5 wt % or below relative to that, more preferably about 2 wt % or below relative to that, the most preferably 1 wt % or below relative to that, for example 0.3 wt % or below relative to that.

The fluoromonomer, which is thermally decomposed according to the process of the present invention, contains PFIB that exhibits a high degree of toxicity together with HFP. The amount of the PFIB, however, is small. Compared with the case where HFP is produced according to the above-mentioned prior art, the amount of the produced PFIB is very small. From that standpoint, the present invention provides a novel process for producing HFP when a fluoromonomer is obtained by thermally decomposing a fluoropolymer as mentioned above. In addition, in the process for producing the HFP according to the present invention, it is possible to produce the HFP with a good yield, inhibiting the generation of PFIB, even if the decomposition temperature of the fluoropolymer is up to 700° C., for example under a low temperature condition of from 600 to 650° C.

INDUSTRIAL APPLICABILITY

According to the present invention, the production of the oligomer, which particularly leads to hindrance to a continuous operation of the thermal decomposition apparatus, can be sufficiently inhibited in the process wherein a fluoropolymer is thermally decomposed to produce a fluoromonomer. In addition, it is possible to inhibit the production of PFIB as a by-product that exhibits a high degree of toxicity, compared with the case with a process for producing HFP based on a conventional thermal decomposition reaction in the gas phase.

EXAMPLES

The present invention will be explained hereinafter more concretely by means of the examples.

The process for producing a fluoromonomer according to the present invention was carried out by using of the rotary kiln apparatus with the rotary kiln furnace as schematically shown in a flow sheet of FIG. 1. The rotary kiln furnace 5 has a heating pipe 6 with a length of 500 mm and a diameter of 100 mm. The heating pipe is constructed such that it is heated from its exterior by means of the electric heaters 7 that enable the temperature setting, disposed separately therearound. Also, the heating pipe is inclined at a angle of about 1° such that a front thereof is lowered relative to a flow direction of the steam. Furthermore, the heating pipe can be rotated at the speed of from 1 to 30 rpm. A mixture of the sandy quartz (of which size was about 3-5 mm) and a fluoropolymer to be thermally decomposed (which was preliminarily pulverized to have a predetermined size (about 3-5 mm)) was continuously supplied from a hopper 2 to the rotary kiln by means of a feeder 4, whereas the steam from a line 3 was heated through a preheater 1, and then it was continuously supplied to the rotary kiln.

The gas produced by the thermal decomposition was entrained with the steam discharged through and from the rotary kiln, and then conducted via a steam discharge 9 to a gas cooling step (not shown) where a quench treatment was carried out. In the gas cooling step, the steam was condensed and a resulting water was removed. The composition of the gas with moisture removed therefrom was determined by gas chromatography. The sandy quartz was recovered into a recovery vessel 7. Such sandy quartz can be returned to the hopper 2 so as to be recycled. The scale-up of the apparatus enables the process of the present invention to be carried out with a similar flow chart from a industrial standpoint.

By means of the above-mentioned rotary kiln, the thermal decomposition of PTFE was carried out under the conditions shown Table 1. The results are also shown in Table 1(in the next page).

C. (examples 4 and 5) respectively. The used steam had an inlet temperature of 600° C. (examples 1-3) or 650° C. (examples 4 and 5), a pressure of 0.1 MPa, an outlet temperature of 600° C. (examples 1-3) or 650° C. (examples 4 and 5). The residence time of the steam was obtained by using of the value of a rotary kiln void volume/a volumetric flow rate of the supplied steam. The amount of the oligomer was obtained by the amount of the oligomer adhered to the wall surface within the steam line 9 (wherein a natural cooling effect took place) which led to a gas cooling step from the rotary kiln.

Under the thermal decomposition conditions according to the example 2, the thermal decomposition step of PTFE produced about 5% oligomer relative to the weight to the resulting product, which, in some cases (e.g. the case where the pipe is narrow or slim), could lead to hindrance to a continuous operation of the thermal decomposition process. However, the amount of the produced oligomer decreases to 2.0% in the example 4 wherein the thermal decomposition temperature is higher. Additionally, the amount of the produced oligomer decreases to 0.3% in the example 5 where the residence time is longer.

This indicates that, on the premise that a high molecular weight fluoropolymer such as PTFE to be introduced to the rotary kiln is thermally decomposed to produce a monomer gas such as TFE as well as a gaseous substance of a low molecular weight polymer (oligomer), when the gaseous substance of oligomer exists under such a temperature atmosphere that it is further thermally decomposed into a monomer gas such as TFE, the residence of the gaseous substance in such atmosphere (i.e. oligomer having a residence time in such atmosphere) is effective in inhibiting a production of the oligomer left behind as a by-product.

The present invention as mentioned above includes the following embodiments:

The first embodiment: the process for producing a fluoromonomer by thermally decomposing a fluoropolymer in a rotary kiln, wherein the fluoropolymer and steam are supplied to the rotary kiln so that the fluoropolymer is heated.

TABLE 1

| Example | Thermal decomposition temperature ° C. | T (K) | Amount of supplied of steam mass ratio | Residence time of steam (t) seconds | $CO_2$ WT % | TFE WT % | HFP WT % | C-318 WT % | PFIB WT % | Other(s) WT % | HFP/PFIB ratio mole ratio | Amount of produced oligomer WT % | T × t K · seconds |
|---|---|---|---|---|---|---|---|---|---|---|---|---|---|
| 1 | 600 | 873 | 4.46 | 5 | 0.53 | 67.1 | 18.1 | 13.0 | 0.34 | 0.93 | 70 | 6.3 | 4365 |
| 2 | 600 | 873 | 2.23 | 10 | 0.40 | 59.0 | 19.4 | 19.5 | 0.43 | 1.27 | 60 | 5.0 | 8730 |
| 3 | 600 | 873 | 0.45 | 50 | 0.46 | 23.0 | 23.5 | 47.9 | 1.01 | 4.13 | 31 | 2.0 | 43650 |
| 4 | 650 | 923 | 2.23 | 10 | 0.60 | 54.1 | 19.5 | 23.4 | 0.65 | 1.75 | 40 | 2.2 | 9230 |
| 5 | 650 | 923 | 0.90 | 25 | 0.95 | 30.6 | 26.3 | 36.6 | 1.65 | 3.90 | 21 | 0.3 | 23075 |

The supplied steam is a ratio by mass of the amount of the supplied steam to the amount of the supplied polymer.
Each composition of the gas is indicated by a mass percentage of the gas (excluding $H_2O$) discharged from the rotary kiln.
The produced oligomer is indicated by a mass percentage based on the amount of the supplied polymer.

The used PTFE, the brand name of which is POLYFLON TFE (manufactured by DAIKIN INDUSTRIES, LTD), was supplied at a rate of 330 g/hr. The supply rate of the sandy quartz was 330 g/hr. The thermal decomposition temperature was obtained by determining the center temperature of the rotary kiln that was divided into three segments. The temperatures at the points that were respectively 5 cm away from the inlet and the outlet of the rotary kiln along the rotation axis thereof, were 590° C. (examples 1-3) and 640°

The second embodiment: the process according to the above first embodiment, wherein the fluoropolymer is a polymer derived from tetrafluoroethylene.

The third embodiment: the process according to the above second embodiment, wherein the polymer derived from tetrafluoroethlene is at least one selected from the group consisting of polytetrafluoroethylene, tetrafluoroethylene/perfluoroalkylvinylether copolymer and tetrafluoroethylene/hexafluoropropylene copolymer.

The fourth embodiment: the process according to any one selected from the first embodiment to the third embodiment, wherein the fluoromonomer is at least one selected from the group consisting of tetrafluoroethylene, hexafluoropropylene and octafluorocyclobutane.

The fifth embodiment: the process according to any one selected from the first embodiment to the fourth embodiment, wherein the steam is supplied to the rotary in such a way that the thermal decomposition is performed at a temperature of from 500 to 700° C. and that an average residence time of the steam is from 5 to 60 seconds.

The sixth embodiment: the process according to any one selected from the first embodiment to the fifth embodiment, wherein the thermal decomposition is performed at a temperature of from 570 to 680° C.

The seventh embodiment: the process according to any one selected from the first embodiment to the sixth embodiment, wherein the thermal decomposition is performed at a temperature of from 620 to 670° C.

The eighth embodiment: the process according to any one selected from the first embodiment to the seventh embodiment, wherein the steam is supplied to the rotary kiln in such a way that an average residence time of the steam is from 10 to 30 seconds.

The ninth embodiment: the process according to any one selected from the first embodiment to the eight embodiment, wherein an amount of a produced oligomer is less than or equal to 2% (by mass) of the fluoropolymer to be thermally decomposed.

The tenth embodiment: the process according to any one selected from the second embodiment to the ninth embodiment, wherein the produced fluoromonomer is such that a mole ratio of hexafluoropropylene/perfluoroisobutene is greater than 20/1.

The eleventh embodiment: the process according to any one selected from the first embodiment to the tenth embodiment, wherein the thermal decomposition is performed in the presence of an inert solid.

The twelfth embodiment: the process according to any one selected from the first embodiment to the eleventh embodiment, which is performed under such a condition that the product (T×t) of the thermal decomposition temperature (T(K), absolute temperature) and the average residence time (t (second)) of the steam within the rotary kiln is at least 9000 (K·seconds).

The present application claims the right of priority of Japanese Application No. 2002-55914 (filed Mar. 1, 2002, the title of the invention: "the process for producing fluoromonomer"), the disclosure of which is all incorporated herein by reference.

The invention claimed is:

1. A process, for producing a fluoromonomer derived from a tetrafluoroethylene polymer comprising:
   supplying a rotary kiln;
   supplying a tetrafluoroethylene polymer to the rotary kiln;
   supplying steam to the rotary kiln;
   heating said tetrafluoroethylene polymer with the steam;
   thermally decomposing said tetrafluoroethylene polymer to a tetrafluroethylene monomer; and
   discharging said tetrafluroethylene monomer from the kiln
   wherein said tetrafluroethylene monomer has a mole ratio of hexafluoropropylene/perfluoroisobutene of greater than 20/1.

2. A process, for producing a fluoromonomer comprising:
   supplying a rotary kiln;
   supplying fluoropolymer to the rotary kiln;
   supplying steam to the rotary kiln;
   heating the fluoropolymer with the steam;
   thermally decomposing the fluoropolymer to the fluoromonomer; and
   discharging the fluoromonomer from the kiln, wherein said process is performed in the presence of an inert solid.

3. A process, for producing a fluoromonomer comprising:
   supplying a rotary kiln;
   supplying fluoropolymer to the rotary kiln;
   supplying steam to the rotary kiln;
   heating the fluoropolymer with the steam;
   thermally decomposing the fluoropolymer to the fluoromonomer; and
   discharging the fluoromonomer from the kiln,
   wherein said process is performed under such a condition that the product (T×t) of a thermal decomposition temperature (T(k), absolute temperature) and an average residence time (t(second)) of the steam within the rotary kiln is at least 9000 (K·seconds).

4. A process, a process for producing a fluoromonomer comprising:
   supplying a rotary kiln;
   supplying fluoropolymer to the rotary kiln;
   supplying steam to the rotary kiln;
   heating the fluoropolymer with the steam;
   thermally decomposing the fluoropolymer to the fluoromonomer;
   entraining the produced fluoromonomer in the steam; and
   discharging the produced fluoromonomer from an interior of the rotary kiln.

5. A process, for producing a fluoromonomer comprising:
   supplying a rotary kiln;
   supplying fluoropolymer to the rotary kiln;
   supplying steam to the rotary kiln;
   heating the fluoropolymer with the steam;
   thermally decomposing the fluoropolymer to the fluoromonomer; and
   discharging the fluoromonomer from the kiln,
   wherein said rotary kiln comprises:
   a cylindrical heating region;
   at least one heating pipe through said rotary kiln;
   a steam line leading to said at least one heating pipe;
   a raw material feeder leading to said cylindrical heating region; and
   a residue recovery vessel at a discharge end of said cylindrical heating region.

6. The process according to claim 5, wherein said steam line additionally comprises a steam preheater.

7. A process, for producing a fluoromonomer comprising:
   supplying a rotary kiln;
   supplying fluoropolymer to the rotary kiln;
   supplying steam to the rotary kiln;
   heating the fluoropolymer with the steam;
   thermally decomposing the fluoropolymer to the fluoromonomer; and
   discharging the fluoromonomer from the kiln, wherein said process is carried out in continuous mode.

8. A process, for producing a fluoromonomer comprising:
   supplying a rotary kiln;
   supplying fluoropolymer to the rotary kiln;
   supplying steam to the rotary kiln;
   heating the fluoropolymer with the steam;
   thermally decomposing the fluoropolymer to the fluoromonomer; and discharging the fluoromonomer from the kiln,
   wherein said process is carried out in batch mode.

9. A process for producing a fluoromonomer comprising:

supplying a rotary kiln;

supplying a solid powder fluoropolymer to the rotary kiln having a longest diameter of 2-5 mm;

supplying steam to the rotary kiln;

heating the fluoropolymer with the steam;

thermally decomposing the fluoropolymer to the fluoromonomer; and discharging the fluoromonomer from the kiln.

* * * * *